United States Patent [19]

Breipohl et al.

[11] Patent Number: 4,922,015

[45] Date of Patent: May 1, 1990

[54] SYNTHESIS OF PEPTIDE AMIDES BY MEANS OF A SOLID PHASE METHOD USING ACID-LABILE ANCHORING GROUPS

[75] Inventors: Gerhard Breipohl, Frankfurt am Main; Jochen Knolle, Kriftel; Werner Stüber, Lahntal, all of Fed. Rep. of Germany

[73] Assignee: Hoechst Aktiengesellschaft, Frankfurt am Main, Fed. Rep. of Germany

[21] Appl. No.: 178,232

[22] Filed: Apr. 6, 1988

[30] Foreign Application Priority Data

Apr. 8, 1987 [DE] Fed. Rep. of Germany ....... 3711866

[51] Int. Cl.⁵ .......................................... C07C 101/30
[52] U.S. Cl. ..................... 562/451; 562/460; 562/468; 560/42; 560/57; 560/52; 530/337
[58] Field of Search ................ 560/36, 42; 562/440, 562/451

[56] References Cited

U.S. PATENT DOCUMENTS 3,825,507  7/1974  Boyd et al. ........................ 562/441

FOREIGN PATENT DOCUMENTS 2114565  8/1983  United Kingdom ................. 562/441

OTHER PUBLICATIONS

J. P. Tam et al, Tetrahedron Lett., vol. 22, pp. 2851–2854, (1981).

C. Ressler et al, J. Am. Chem. Soc., vol. 76, pp. 3107–3109 (1954).

Primary Examiner—James H. Reamer
Attorney, Agent, or Firm—Finnegan, Henderson, Farabow, Garrett and Dunner

[57] ABSTRACT

The invention relates to new compounds of the formula

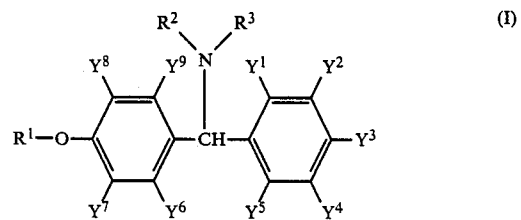

in which $R^1$ denotes $(C_1-C_8)$-alkyl or optionally substituted $(C_6-C_{14})$-aryl, $R^2$ denotes hydrogen or an amino acid residue which is protected by an amino protective group which can be cleaved off with weak acid or base, $R^3$ denotes hydrogen or $(C_1-C_4)$-alkyl, and $Y^1$-$Y^9$ denote identical or different radicals hydrogen, $(C_1-C_4)$-alkyl, $(C_1-C_4)$-alkoxy or $-O-(CH_2)_n-COOH$ (with $n=1$ to 6), one of these radicals being $-O-(CH_2)_n-COOH$. A process for the preparation thereof and the synthesis of peptide amides by means of a solid phase method using these new compounds (spacers) are described.

12 Claims, No Drawings

SYNTHESIS OF PEPTIDE AMIDES BY MEANS OF A SOLID PHASE METHOD USING ACID-LABILE ANCHORING GROUPS

The invention relates to new spacers and processes for the preparation thereof, and to the synthesis of peptide amides by means of a solid phase method using these acid-labile anchoring groups.

Generally used for the preparation of peptide amides by means of solid phase synthesis are benzhydrylamine resins or methylbenzhydrylamine resins as are described in, for example, J. P. Tam et al., Tetrahedron Lett. 22, 2851 (1981). Another method comprises the ammonolysis of carrier-bound peptide benzyl esters (C. Ressler et al., J. Am. Chem. Soc. 76, 3107 (1951)). Features of both methods are the strong acid (liquid hydrogen fluoride or trifluoromethanesulfonic acid) necessary for cleaving off the spacer, side reactions or incomplete cleavage off.

Hence the invention is based on the object of finding new spacers which allow milder and better cleavage of peptide amides off from the carrier resin.

This object is achieved according to the invention by the compounds of the general formula I

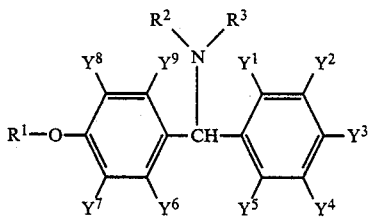

in which $R^1$ denotes $(C_1–C_8)$-alkyl or optionally substituted $(C_6–C_{14})$-aryl, $R^2$ denotes hydrogen or an amino acid residue which is protected by an amino protective group which can be cleaved off with weak acid or base, $R^3$ denotes hydrogen or $(C_1–C_4)$-alkyl, $Y^1$, $Y^2$, $Y^3$, $Y^4$, $Y^5$, $Y^6$, $Y^7$, $Y^8$ and $Y^9$ denote hydrogen, $(C_1–C_4)$-alkyl, $(C_1–C_4)$-alkoxy or $-O-(CH_2)_n-COOH$, it being possible for the radicals to be identical or different but one radical being $-O-(CH_2)_n-COOH$, and n denotes an integer from 1 to 6.

Preferred compounds of the general formula I are those in which $R^1$ is methyl and n is the integer 1, 2 or 3.

Likewise preferred compounds of this general formula I in which $R^2$ denotes an amino acid residue which is protected with a urethane protective group, in particular Fmoc, and $R^3$ denotes hydrogen.

Furthermore, the radicals $Y^1-Y^9$ represent, in particular, methyl or methoxy, with, however, one radical being $-O-(CH_2)_n-COOH$ and at least 4 of these radicals being hydrogen.

It is preferred for $Y^1$, $Y^3$, $Y^5$, $Y^7$ or $Y^8$ to represent the radical $-O-(CH_2)_n-COOH$.

Alkyl and alkoxy can be straight-chain or branched.

Examples of $(C_6–C_{14})$-aryl are phenyl, naphthyl, biphenylyl or fluorenyl; phenyl is preferred.

$R^2$ represents the residue of an amino acid, preferably of an α-amino acid which, if chiral, may be in the D- or L-form. Preferred residues are those of naturally occurring amino acids, their enantiomers, homologs, derivatives and simple metabolites (cf., for example, Wünsch et al., Houben-Weyl 15/1 and 2, Stuttgart, Thieme 1974). Thus, the following are suitable examples:

Aad, Abu, YAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, Cyta, Daad, Dab, Dadd, Dap, Dapm, Dasu, Djen, Dpa, Dtc, Fel, Gln, Glu, Gly, Guv, hCys, His, hSer, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val and the residues of the corresponding enantiomeric D-amino acids.

Functional groups in the side chains of the said amino acid residues can be protected. Suitable protective groups are described by Hubbuch, Kontakte (Merck) 1979, No. 3, pages 14–23, and by Bullesbach, Kontakte (Merck) 1980, No. 1, pages 23–35.

Protective groups which are base-labile or labile to weak acids are, in particular, urethane protective groups such as Fmoc, Ddz, Bpoc, Msc, Peoc, Pse and Tse, preferably Fmoc (see, for example, Hubbuch, Kontakte (Merck) 1979, No. 3, pages 14–23).

The invention also relates to a process for the preparation of the compounds of the formula I, which comprises (a) reaction of a compound of the formula II

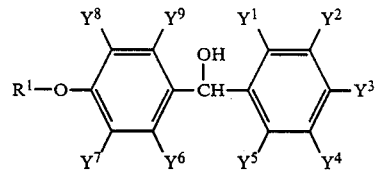

in which $R^1$ denotes $(C_1–C_8)$-alkyl or optionally substituted $(C_6–C_{14})$-aryl, $Y^1$, $Y^2$, $Y^3$, $Y^4$, $Y^5$, $Y^6$, $Y^7$, $Y^8$ and $Y^9$ denote hydrogen, $(C_1–C_4)$-alkyl, $(C_1–C_4)$-alkoxy or $-O-(CH_2)_n-COOH$, it being possible for the radicals to be identical or different but one radical being $-O-(CH_2)_n-COOH$, and n denotes an integer from 1 to 6, with a compound of the formula III

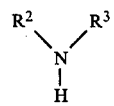

in which $R^2$ denotes hydrogen or an amino acid residue which is protected by an amino protective group which can be cleaved off by weak acid or base, and $R^3$ denotes hydrogen or $(C_1–C_4)$-alkyl, or (b) reaction of a compound of the formula IV

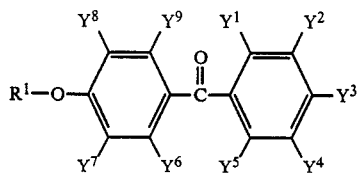

(IV)

with hydroxylamine to give a compound of the formula V

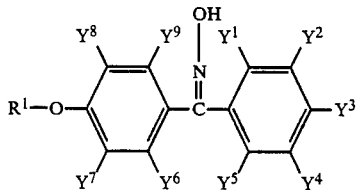

(V)

in which $R^1$, $Y^1$, $Y^2$, $Y^3$, $Y^4$, $Y^5$, $Y^6$, $Y^7$, $Y^8$ and $Y^9$ are as defined above, then reduction of the oxime to the amine, preferably with zinc in glacial acetic acid (S. Gaehde, G. Matsueda, Int. J. Peptide Protein Res. 18, 451 (1981)) and, where appropriate, conversion into its derivatives.

The reaction of a compound of the formula II with a compound of the formula III is preferably carried out in a polar protic solvent, such as, for example, acetic acid, at a temperature between 0° C. and the boiling point of the reaction mixture.

The compounds of the formula II are new.

Compounds of the formula II are obtained, for example, by reduction of benzophenone derivatives of the formula IV

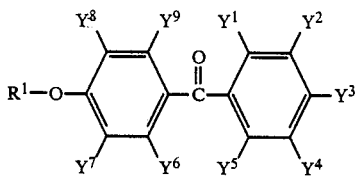

(IV)

in which $R^1$, $Y^1$, $Y^2$, $Y^3$, $Y^4$, $Y^5$, $Y^6$, $Y^7$, $Y^8$ and $Y^9$ are as defined above, with suitable reducing agents, i.e. selective for the keto group, such as, for example, sodium borohydride.

Benzophenone derivatives of the formula IV are obtained (a) by reaction of benzophenones of the formula IV, in which $R^1$ is as defined above, and $Y^1$, $Y^2$, $Y^3$, $Y^4$, $Y^5$ $Y^6$, $Y^7$, $Y^8$ and $Y^9$ denote hydrogen, ($C_1$–$C_4$)-alkyl or ($C_1$–$C_4$)-alkoxy, and one of the radicals $Y^1$–$Y^9$ denotes hydroxyl, with ω-halogeno fatty acids of the formula VI $$Hal-(CH_2)_n-COOH \qquad (VI)$$

in which Hal denotes halogen, and n is as defined above, or the esters thereof, there being, in the case of the esters, subsequent alkaline hydrolysis of the ester group, for example with sodium hydroxide solution (M. Prashad et al., Indian J. Chem. 17B, 496–498 (1979)).

(b) for example by reaction of benzoyl chlorides of the formula VII

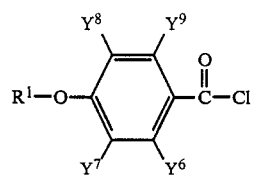

(VII)

with ω-phenoxyalkanoic acids of the formula VIII

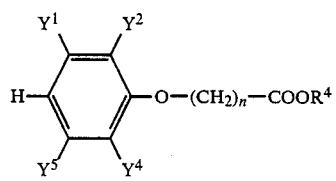

(VIII)

in which $R^1$, $Y^1$, $Y^2$, $Y^4$, $Y^5$, $Y^6$, $Y^7$, $Y^8$, $Y^9$ and n are as defined under (a), and $R^4$ denotes ($C_1$–$C_8$)-alkyl, preferably methyl or ethyl, with use of a Lewis catalyst such as, for example, aluminum trichloride or titanium tetrachloride (Organikum, 13th edition, page 354 (1974)), or (c) by reaction of the appropriate benzoyl chloride of the formula VII with appropriately substituted phenols of the formula IX to give the corresponding phenyl esters of the formula X

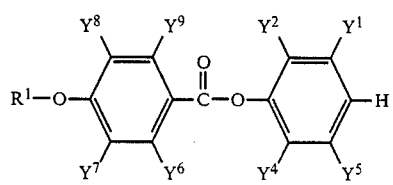

(X)

subsequent Fries isomerization with Lewis acids such as, for example, titanium tetrachloride (R. Martin et al., Monatsh. Chemie 110, 1057–1066 (1979)) and further reaction with ω-halogeno fatty acids of the formula VI, in which Hal and n are as defined above.

Compounds of the formula VIII are prepared by reaction of the corresponding phenols of the formula IX

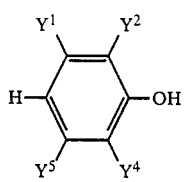

(IX)

with the appropriate ω-halogenoalkanoic esters, for example with sodium hydride in dimethylformamide (DMF) or potassium carbonate in acetone.

It is also possible to prepare the compounds of the formulae VII, VIII, IX and X corresponding to the general formula I analogously.

The invention furthermore relates to the use of a compound of the formula I in which $R^2$ does not denote hydrogen in the solid phase synthesis of compounds of the formula XI $$P-R^2-NH-R^3 \qquad (XI)$$

in which P represents a peptide residue composed of $q \leq p+1$ α-amino acids, $R^2$ denotes an amino acid residue which is protected with an amino protective group which can be cleaved off with weak acid or base, and $R^3$ is as defined above, and to a process for the preparation of a peptide of the formula XI in which P, $R^2$ and $R^3$ are as defined above, by solid phase synthesis, which comprises coupling a compound of the formula I, using coupling reagents customary in peptide chemistry, via the —O—$(CH_2)_n$—COOH group to a resin, cleaving off the protective group on the amino acid $R^2$, stepwise coupling on of q-p α-amino acids which are, where appropriate, in the form of their activated derivatives and have been temporarily protected by amino protective groups which are base-labile or labile to weak acids, and, after the synthesis is complete, liberation of the peptide of the formula XI from the resin by treatment with a moderately strong acid, with temporarily introduced side-chain protective groups being cleaved off again at the same time or by suitable measures subsequent thereto.

If necessary to prevent side reactions or for the synthesis of specific peptides, the functional groups in the side chain of amino acids will be additionally protected by suitable protective groups (see, for example, T. W. Greene, "Protective Groups in Organic Synthesis", New York, John Wiley & Sons, 1981), those primarily used being Arg(Tos), Arg(Mts), Arg(Mtr), Asp(OBzl), Asp(OBut), Cys(4-MeBzl), Cys(Acm), Cys(SBut), Glu(OBzl), Glu(OBut), His(Tos), His(Fmoc), His(Dnp), His(Trt), Lys(Cl-2), Lys(Boc), Met(O), Ser(Bzl), Ser(But), Thr(Bzl), Thr(But)

The resins used as carrier material are commercially available or prepared by us, such as, for example, alkoxybenzyl alcohol resins, aminomethyl resins or benzhydrylamino resins. Benzhydrylamino resins (BHA) and methyl-O benzhydrylamino resins (MBHA) are preferred. The loading is determined by amino acid analysis and/or elemental analysis.

It is possible to use as coupling reagent for the compound of the formula I and the further amino acid derivatives all possible activating reagents used in peptide synthesis, see, for example, Houben-Weyl, Methoden der organischen Chemie (Methods of Organic Chemistry), volume 15/2, but especially carbodiimides such as, for example, N,N'-dicyclohexylcarbodiimide, N,N'-diisopropylcarbodiimide or N-ethyl-N'-(2-dimethylaminopropyl)carbodiimide. This coupling can be carried out directly by addition of amino acid derivative with the activating reagent and, where appropriate, an additive suppressing racemization, such as, for example, 4-dimethylaminopyridine, 1-hydroxybenzotriazole (HOBt) (W. König, R. Geiger, Chem. Ber. 103, 708 (1970)) or 3-hydroxy-4-oxo-3,4-dihydrobenzotriazine (HOObt) (W. König, R. Geiger, Chem. Ber. 103, 2054 (1970)) to the resin, or the preactivation of the amino acid derivative as symmetric anhydride or HOBt or HOObt ester can be carried out separately, and the solution of the activated species in a suitable solvent can be added to the peptide-resin which is ready for coupling.

The coupling and activation of the compound of the formula I and the amino acid derivatives using one of the abovementioned activating reagents can be carried out in dimethylformamide or methylene chloride or a mixture of the two. The activated amino acid derivative is normally used in a 1.5- to 4-fold excess. In cases where incomplete coupling occurs, the coupling reaction is repeated without previously carrying out the unblocking of the α-amino group of the peptide-resin which is necessary for the coupling of the next amino acid in the sequence.

Successful completion of the coupling reaction can be checked by means of the ninhydrin reaction as described, for example, by E. Kaiser et al. Anal. Biochem. 34 595 (1970). The synthesis can also be carried out automatically, for example using a model 430A peptide synthesizer from Applied Biosystems, it being possible to use either the synthesis programs provided by the manufacturer of the apparatus or those constructed by the user himself. The latter are particularly employed when using amino acid derivatives protected with the Fmoc group.

The peptide amides are cleaved off from the resin by treatment with moderately strong acids customarily used in peptide synthesis (for example trifluoroacetic acid), with the addition, as cation traps, of substances such as phenol, cresol, thiocresol, anisole, thioanisole, ethanedithiol, dimethyl sulfide, ethyl methyl sulfide or similar cation traps customary in solid phase synthesis, singly or a mixture of two or more of these auxiliaries. In this connection, the trifluoroacetic acid can also be employed diluted with suitable solvents such as, for example, methylene chloride. The side-chain protective groups are cleaved off at the same time as the spacer is cleaved off from the resin.

The crude peptides obtained in this way are purified by means of chromatography on Sephadex ®, ion exchanger resins or HPLC.

The examples which follow serve to illustrate the present invention without intending to restrict it to them.

EXAMPLE 1

Methyl 4-(4-methoxybenzoyl)phenoxyacetate 64 g of aluminum chloride (anhydrous) are dissolved in 160 ml of 1,2-dichloroethane, and 71.6 g of 4-methoxybenzoyl chloride are added. 57.6 ml of methyl phenoxyacetate are slowly added dropwise, while stirring, and the reaction mixture is heated at 50° C. for 4 hours. The mixture is added dropwise to ice-water, during which an oil separates out. The aqueous phase is separated off, and the residue is extracted three times by stirring with water and is crystallized using methanol. The precipitate is filtered off and recrystallized from ethyl acetate.

Yield: 54.9 g (53% of theory)

Melting point: 146° C. (148° C., ethyl acetate)

EXAMPLE 2

4-(4-Methoxybenzoyl)phenoxyacetic acid 9.0 g of the methyl ester (Example 1) are dissolved in 120 ml of 1,2-dimethoxyethane/water (4:1, v:v), and 15 ml of 2N NaOH are added. The mixture is stirred for three hours, and the pH is adjusted to 3 with 3N HCl. The organic solvent is evaporated off in vacuo, and the precipitated product is filtered off, washed with water and dried under high vacuum.

Yield: 8.4 g (98% of theory)

Melting point: 181°–182° C.

EXAMPLE 3

(4-Carboxymethoxyphenyl)-4-methoxyphenylcarbinol 11.2 g of 4-(4-methoxybenzoyl)phenoxyacetic acid are dissolved in 600 ml of 80% strength methanol (reflux), and 4.4 ml of N-methylmorpholine are added. 6 g of sodium borohydride are added in portions over the course of two hours, and the reaction is continued under reflux conditions for 3 hours. The mixture is cooled to room temperature and acidified to pH 2.5 with 3N HCl. The methanol is distilled off, the aqueous phase is extracted with ethyl acetate, and the organic phase is washed with brine and dried over sodium sulfate. After removal of the ethyl acetate by distillation there remains a white amorphous powder. The product is used directly for the next reaction.

Yield: 9.3 g (83% of theory)

EXAMPLE 4

Methyl 2-methylphenoxyacetate 108 g of 2-methylphenol are dissolved in 500 ml of dry acetone, and 165.8 g of powdered potassium carbonate are added. 113 ml of methyl bromoacetate are added to the stirred suspension, and the mixture is left to stir at room temperature with exclusion of moisture. After the reaction is complete, the salt is filtered off with suction and washed with acetone, and the filtrate is concentrated. The residue is taken up in ethyl acetate, and the organic phase is washed with water, dried over magnesium sulfate and concentrated.

Yield: 180 g of an oily liquid which is immediately reacted further.

EXAMPLE 5

Methyl 4-(4-methoxybenzoyl)-2-methylphenoxyacetate 146.6 g of anhydrous aluminum trichloride are dissolved in 500 ml of 1,2-dichloroethane. At 0° C., 187 g of 4-methoxybenzoyl chloride and 180 g of methyl 2-methylphenoxy acetate are successively added dropwise. The mixture is heated at 50° C. to complete the reaction. It is poured onto ice and the pH is adjusted to 2 with 2N HCl. The precipitated product is filtered off with suction and washed with water and a little ether. The precipitate is dissolved in hot ethyl acetate with the addition of a little active charcoal, and the mixture is filtered and crystallization is carried out at −10° C. The product is filtered off with suction, washed with ether and dried under high vacuum.

Yield: 172.8 g (55% of theory)
Melting point: 92°–95° C.

EXAMPLE 6

Methyl 4-(4-methoxybenzoyl)-2-methylphenoxyacetate 50 g of 4-hydroxy-3-methyl-4′-methoxybenzophenone (R. Martin et al. Monatsh. Chemie 110, 1057–1066 (1979)) are dissolved in 200 ml of dry DMF and, under $N_2$, 9 g of a 55% dispersion of sodium hydride in mineral oil are cautiously added. Then, while stirring, 19.5 ml of methyl bromoacetate are added dropwise, and the mixture is left to stand at room temperature overnight. The precipitated salt is filtered off with suction, and the filtrate is concentrated in vacuo. The residue is taken up in ethyl acetate, and the solution is washed with sodium bicarbonate solution and water. The organic phase is dried over magnesium sulfate, and the solvent is removed in vacuo. The residue is triturated with ether, filtered off with suction and dried.

Yield: 38.9 g (60% of theory)
Melting point: 96°–98° C.

EXAMPLE 7

Methyl 4-(4-methoxybenzoyl)-phenoxyacetate 29.1 g of 4-hydroxy-4′-methoxybenzophenone (R. Martin et al., Monatsh, Chemie 110, 1057–1066 (1979)) are dissolved in 400 ml of dry acetone. Then, while stirring, 19.3 g of finely powdered $K_2CO_3$ and 16 ml of methyl bromoacetate are added, and the mixture is stirred at room temperature. The reaction is complete after 2 days. The precipitated mixture of salt and substance is filtered off with suction, and the filtrate is concentrated. Both residues are suspended in water, and the pH is adjusted to 3 with 2N HCl. The solid is filtered off with suction, washed with water and dried under high vacuum in a desiccator.

Yield: 35.7 g (98% of theory)
Melting point: 143°–145° C.

EXAMPLE 8

4-(4-Methoxybenzoyl)-2-methylphenoxyacetic acid 35.8 g of methyl 4-(4-methoxybenzoyl)-2-methylphenoxyacetate are stirred with a mixture of 240 ml of dioxane and 240 ml of 0.5N NaOH at room temperature. After the reaction is complete, the organic solvent is removed in vacuo, and the aqueous phase is adjusted to pH 3 with 2N HCl and extracted with ethyl acetate. The organic phase is washed with water, dried over magnesium sulfate and concentrated. Pale yellow crystals remain.

Yield: 30.2 g (83% of theory)
Melting point: 149°–151° C.

EXAMPLE 9

(4-Carboxymethoxy-3-methylphenyl)-4-methoxyphenylcarbinol 22.5 g of 4-(4-methoxybenzoyl)-2-methylphenoxyacetic acid are dissolved in a mixture of 100 ml of dioxane and 200 ml of water, adding 1N NaOH to pH 9. 2.8 g of sodium borohydride are added in portions to the stirred solution, and the mixture is left to stand overnight. The dioxane is then removed in vacuo, and the aqueous phase is adjusted to pH 3 with 2N HCl and extracted with ethyl acetate. The organic phase is dried over magnesium sulfate and concentrated. A colorless foam remains and is triturated with n-hexane to give an amorphous powder which is then filtered off with suction. The product is used directly for the next reaction.

Yield: 19.2 g (84% of theory)

EXAMPLE 10

Methyl 2,6-dimethylphenoxy acetate 65 g of 2,6-dimethylphenol are dissolved in 200 ml of dry DMF and, under $N_2$, 23.2 g of a 55% suspension of sodium hydride in mineral oil are added in portions. Then 50.4 ml of methyl bromoacetate are added dropwise with stirring, and the mixture is left to stand overnight. The precipitated salt is filtered off with suction, and the filtrate is concentrated. The residue is taken up in ethyl acetate, and the solution is extracted with water. The organic phase is dried over magnesium sulfate and concentrated. An oily liquid remains and is used directly in the following reaction.

Yield: 95.8 g (92% of theory)

EXAMPLE 11

Methyl 2,6-dimethyl-4-(4-methoxybenzoyl)phenoxyacetate

The synthesis is carried out in analogy to Example 5 using 19.4 g of methyl 2,6-dimethylphenoxyacetate.

Yield: 17.4 g (53% of theory)

EXAMPLE 12

(4-Carboxymethoxy-3,5-dimethylphenyl)-4-methoxyphenylcarbinol 16.4 g of methyl 2,6-dimethyl-4-(4-methoxybenzoyl)-phenoxyacetate are stirred in a mixture of 100 ml of 0.5N NaOH and 100 ml of dioxane at room temperature. After the hydrolysis of the methyl ester is complete, 1.89 g of sodium borohydride are added, and the mixture is left to react overnight. Then a little insoluble material is filtered off with suction, the filtrate is concentrated, and the remaining aqueous solution is acidified with 1N HCl. It is extracted with ethyl acetate, and the organic phase is washed with water, dried over magnesium sulfate and concentrated. An amorphous powder remains and is used directly for the subsequent reaction.

Yield: 11.3 g (71% of theory)

General procedure for the preparation of the (4-carboxymethoxyphenyl)-4-methoxyphenylmethylamides of Nα-Fmocamino acids, and of the (4-carboxymethoxy-3-methylphenyl)- 4-methoxyphenylmethylamides of Nα-Fmoc-amino acids and of (4-carboxymethoxy-3,5-dimethylphenyl)-4-methoxyphenylmethylamides of Nα-Fmoc-amino acids.

10 mmol of Nα-Fmoc-amino acid amide and 10 mmol of the appropriate carbinol are dissolved in the required amount of glacial acetic acid, and 5–10 drops of concentrated sulfuric acid are added. 2 g of molecular sieves are also added, and the mixture is left to stand overnight. The molecular sieves are then filtered off with suction, and the filtrate is diluted with a large amount of water, when part of the product precipitates out. The aqueous phase is extracted with ethyl acetate, and then the organic phase is extracted by shaking with water. The substance remaining after drying over magnesium sulfate and concentration is recrystallized.

The following compounds were prepared by the abovementioned general procedure:

EXAMPLE 13

(4-Carboxymethoxyphenyl)-4-methoxyphenylmethylamide of Nα-Fmoc-glycine

Yield: 65%
Melting point: 136°–138° C.

EXAMPLE 14

(4-Carboxymethoxyphenyl)-4-methoxyphenylmethylamide of Nα-Fmoc-phenylalanine

Yield: 65%
Melting point: 159°–162° C.

EXAMPLE 15

(4-Carboxymethoxy-3-methylphenyl)-4-methoxyphenylmethylamide of Nα-Fmoc-glycine

Yield: 60%

Melting point: 135°–140° C.

EXAMPLE 16

(4-Carboxymethoxy-3-methylphenyl)-4-methoxyphenylmethylamide of Nα-Fmoc-valine

Yield: 81%
Melting point: 172°–175° C.

EXAMPLE 17

(4-Carboxymethoxy-3,5-dimethylphenyl)-4-methoxyphenylmethylamide of Nα-Fmoc-glycine Yield: 70%
Melting point: 122°–126° C.

EXAMPLE 18

Synthesis of oxytocin

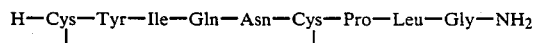

using the anchor described in Example 13. The synthesis was carried out in a peptide synthesizer supplied by Labotec.

Firstly, the protective group is removed from 1.5 g of Boc-Val-resin (loading 0.76 mmol/g) using trifluoroacetic acid in methylene chloride. The resin is washed with dichloromethane and ethyldiisopropylamine and again with dichloromethane and then dried. 2.1 mmol of the anchor prepared in Example 13 are then added, together with 3.15 mmol of HOBt dissolved in 20 ml of dry DMF, to the resin, and 2.3 mmol of diisopropylcarbodiimide are added. The mixture is left to react at room temperature overnight, stirring slowly. The ninhydrin reaction (Kaiser test) is used to check that the reaction is complete. The resin is then filtered off with suction and washed with DMF, and the peptide is subsequently synthesized on the resin, carrying out the following steps in cycles:

Fmoc protective group cleaved off with 20% piperidine in DMF resin washed with DMF Fmoc-amino acid coupled on with in situ activation as HOBt ester and using diisopropylcarbodiimide as activating reagent (2.1 mmol of amino acid, 3.15 mmol of HOBt, 2.3 mmol of diisopropylcarbodiimide)

resin washed with DMF.

If the coupling is incomplete (Kaiser test), the coupling step is repeated.

The side-chain protective groups used are tert.-butyl for tyrosine and tert.-butylthio for cystein.

After the synthesis is complete, first the Fmoc protective group is cleaved off, and then the resin is successively washed with DMF, dichloromethane, isopropanol, dichloromethane and tert.-butyl methyl ether, and is dried under high vacuum. 2.4 g of peptide-resin are obtained. Cleavage of this is carried out at room temperature using a mixture of trifluoroacetic acid/thioanisole/ethanedithiol (80/15/5). After 2 hours, the mixture is filtered with suction into tert.-butyl methyl ether, and the precipitated crude peptide is removed by centrifugation and washed three times with tert.-butyl methyl ether. The tert.-butylthio protective group is cleaved off by tributylphosphine in trifluoroethanol/water at pH 7.3. The S-H peptide is cyclized with iodine in 60% strength acetic acid and is purified by chromatography on Sephadex ® LH 20 in methanol.

Yield of oxytocin 33%, identical to an authentic comparison sample.

We claim:

1. A compound of the formula I

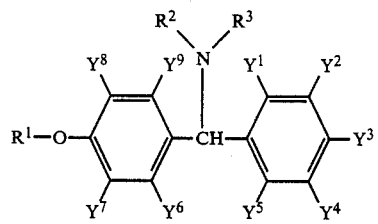

in which
- R¹ denotes (C₁–C₈)-alkyl, (C₆–C₁₄)-aryl or substituted (C₆–C₁₄)-aryl,
- R² denotes hydrogen or an amino acid residue which is protected by an amino protective group which can be cleaved off with weak acid or base,
- R³ denotes hydrogen or (C₁–C₄)-alkyl,
- Y¹, Y², Y³, Y⁴, Y⁵, Y⁶, Y⁷, Y⁸ and Y⁹ denote hydrogen, (C₁–C₄)-alkyl, (C₁–C₄)-alkoxy or —O—(CH₂)ₙ—COOH, it being possible for the radicals to be identical or different but a singles radical being —O—(CH₂)ₙ—COOH, and
- n denotes an integer from 1 to 6.

2. A compound of the formula I as claimed in claim 1, in which R¹ is methyl, and n is an integer 1, 2 or 3.

3. A compound of the formula I as claimed in claim 1, in which R² denotes an amino acid residue which is protected with a urethane protective group, and R³ denotes hydrogen.

4. A compound of the formula I as claimed in claim 1, in which the radicals Y¹, Y², Y³, Y⁴, Y⁵, Y⁶, Y⁷, Y⁸, and Y⁹ represent methyl or methoxy with a single radical being —O—(CH₂)ₙ—COOH and at least 4 of these radicals denoting hydrogen.

5. A compound of the formula I as claimed in claim 1, in which the radicals Y¹, Y³, Y⁵, Y⁷ or Y⁸ represents —O—(CH₂)ₙ—COOH.

6. A compound of the formula I as claimed in claim 1, in which
- R¹ is (C₁–C₈)-alkyl,
- R² denotes an α-amino acid residue which is protected with an urethane protective group,
- R³ denotes hydrogen,
- Y¹, Y², Y³, Y⁴, Y⁵, Y⁶, Y⁷, Y⁸ and Y⁹ denote hydrogen, methyl or —O—(CH₂)ₙ—COOH, it being possible for the radicals to be identical or different but a single radical being —O—(CH₂)ₙ—COOH and at least 6 of these radicals being hydrogen, and
- n is an integer 1, 2 or 3.

7. A compound of the formula I as claimed in claim 1, in which
- R¹ is methyl,
- R² denotes Gly, Val or Phe which are protected with a Fmoc group,
- R³ denotes hydrogen,
- Y¹, Y⁵, Y⁶, Y⁷, Y⁸ and Y⁹ denote hydrogen,
- Y² and Y⁴ are identical or different and denote hydrogen or methyl,
- Y³ denotes —O—(CH₂)ₙ—COOH, and
- n is 1.

8. The compound of the formula I as defined in claim 1, which is (4-carboxymethoxyphenyl)-4-methoxyphenylmethylamide of Nα-Fmoc-glycine.

9. The compound of the formula I as defined in claim 1, which is (4-carboxymethoxyphenyl)-4-methoxyphenylmethylamide of Nα-Fmoc-phenylalanine.

10. The compound of the formula I as defined in claim 1, which is (4-carboxymethoxy-3-methylphenyl)-4-methoxyphenylmethylamide of Nα-Fmoc-glycine.

11. The compound of the formula I as defined in claim 1, which is (4-carboxymethoxy-3-methylphenyl)-4-methoxyphenylmethylamide of Nα-Fmoc-valine.

12. The compound of the formula I as defined in claim 1, which is (4-carboxymethoxy-3,5-dimethylphenyl)-4-methoxyphenylmethylamide of Nα-Fmoc-glycine.

* * * * *

UNITED STATES PATENT AND TRADEMARK OFFICE
CERTIFICATE OF CORRECTION

PATENT NO. : 4,922,015

DATED : May 01, 1990

INVENTOR(S) : Gerhard BREIPOHL et al.

It is certified that error appears in the above-identified patent and that said Letters Patent is hereby corrected as shown below:

Claim 1, Column 11, Line 28, change "singles" to --single--.

Claim 5, Column 12, Line 2, change "the radicals" to --a single radical--.

Signed and Sealed this

Fifteenth Day of September, 1992

Attest:

DOUGLAS B. COMER

*Attesting Officer*      *Acting Commissioner of Patents and Trademarks*